United States Patent [19]

Antoine

[11] Patent Number: 4,811,591
[45] Date of Patent: Mar. 14, 1989

[54] DEVICE FOR CHECKING THE SURFACE CONDITION OF MATERIALS

[76] Inventor: Antoine Antoine, F-08370 La Ferte Sur Chiers, France

[21] Appl. No.: 101,293
[22] PCT Filed: Jan. 12, 1987
[86] PCT No.: PCT/FR87/00008
§ 371 Date: Sep. 10, 1987
§ 102(e) Date: Sep. 10, 1987
[87] PCT Pub. No.: WO87/04235
PCT Pub. Date: Jul. 16, 1987

[30] Foreign Application Priority Data

Jan. 13, 1986 [FR] France ................... 8600470

[51] Int. Cl.$^4$ .................. G01N 19/02; G01N 19/04
[52] U.S. Cl. ........................................ 73/9; 73/105
[58] Field of Search ............. 73/105, 104, 8, 9, 150 A, 73/146

[56] References Cited

U.S. PATENT DOCUMENTS

| | | |
|---|---|---|
| 3,017,618 | 1/1962 | Cross .......................... 15/104.063 |
| 3,893,330 | 7/1975 | Shute et al. ...................... 73/8 |
| 3,935,468 | 1/1976 | Bowen et al. . | 
| 4,051,713 | 10/1977 | Bao et al. . |
| 4,098,111 | 7/1978 | Hardmärk et al. ..................... 73/9 |
| 4,106,333 | 8/1978 | Salje et al. . |
| 4,662,211 | 5/1987 | Strong ..................... 73/9 |

FOREIGN PATENT DOCUMENTS

| | | |
|---|---|---|
| 2627239 | 12/1976 | Fed. Rep. of Germany . |
| 2947259 | 5/1981 | Fed. Rep. of Germany . |
| 1460033 | 10/1966 | France . |

*Primary Examiner*—Stewart J. Levy
*Assistant Examiner*—Robert P. Bell
*Attorney, Agent, or Firm*—Cushman, Darby & Cushman

[57] ABSTRACT

The invention pertains to a device for checking the surface condition of materials. The disclosed device is essentially comprised of an adherence measuring sensor whose sensitive element is set in contact with the surface of the material, in relative motion with respect with said surface, and an associated computer which provides for the comparative measurement, the display and the possible piloting of the surface treatment or production apparatus. The sensor comprises two wheels (1 and 2) mounted on fluid bearings (3) and rolling on the material (4) of which the surface condition is to be controlled and devices (5 and 6) for measuring the speed differential, of the wheels (1 and 2) and providing for the progressive braking of one of the wheels (2).

9 Claims, 1 Drawing Sheet

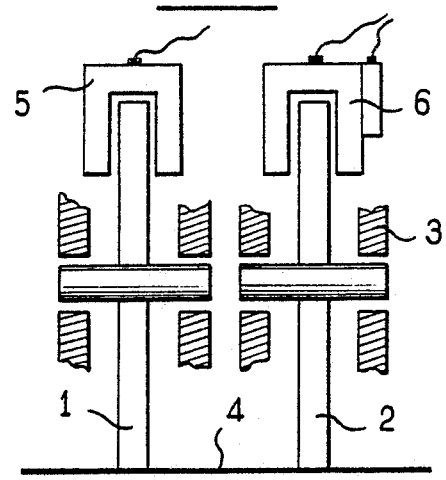
FIG_1
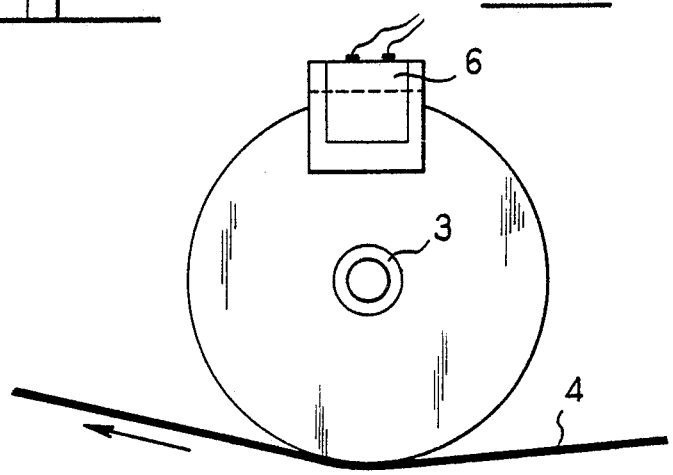
FIG_2
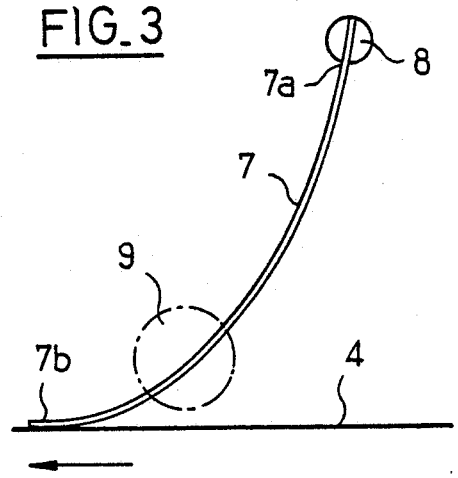
FIG_3

DEVICE FOR CHECKING THE SURFACE CONDITION OF MATERIALS

The invention pertains to a device for checking the surface condition of materials.

As part of their final treatment, certain materials must be coated with a layer of another material for protection, for changing their appearance or for subsequent assembly with similar or different materials. The bonding strength of this layer primariliy depends on the surface condition of the materials being coated; however, often the surface condition does not meet the requirements for high quality bonding and special intermediate treatment is necessary.

Although a wide range of mechanical, chemical, heat, electronic and X-ray treatments are available for surfaces, the inspection resources for checking their effectiveness have been until now rather empirical, discontinuous and destructive and they all have required samples of the material.

With this type of inspection equipment, no automatic and continuous control of a surface treatment is possible during its application.

This situation results in signficant scrapping, regardless of how often the controls are performed and the care exercised, and requires frequent interventions by qualified personnel.

A device for controlling the surface condition of materials has already been described in German Pat. No. DE-A-2 535 912, which pertains to a surface roughness indicator, based mainly on the conversion of a well known technique, used for the retransmission of sound signals recorded by means of surface asperities on the bottom of record grooves, to the field of mechanics in order to transform the surface roughness into variations of an electrical signal, which, in this case, are plotted on a cathode ray tube or stored on a recorder.

The indicating device consists of a rigid arm, fitted with a needle and connected to a support via a flexible hinge, which transmits back the amplitude variations on the metal part being controlled to a rigid lever via a control rod. The lever movement activates a commonly used device, such as a solenoid subject to a varying magnetic flux after a change in position of the magnetic core, coupled to the aforementioned lever, or other similar devices. To ensure that the surface roughness is accurately transmitted to the receiver, both the lever and the arm must embody high stiffness and the needle tip must be sufficiently pointed. This means that the use of the device is restricted to hard materials.

The purpose of the present invention is to overcome these drawbacks. As described in these patent claims, this invention solves this difficulty by the creation of a device capable of relative, continuous or discontinuous measurements of the surface condition of the material that are made directly on the material without the need for samples. This is accomplished by means of a device comprising: an adhesion measuring sensor, the sensing element of which is maintained in contact with the surface of the material subject to surface roughness control and which is in relative motion with respect to the surface; and a computer, which performs the comparative measurements and display functions and which can control the surface treatment facility if necessary.

The advantages resulting from this invention consist mainly of the fact that the surface condition is determined sequentially and directly on materials in motion, or by moving the sensor relative to the material, and that the measurement results are used directly for controlling the surface treatment facility.

Details of this invention are presented below and illustrated by drawings showing two possible embodiments of a device for checking a surface treatment facility employing corona conduction on films of plastic material, product at high speed (60–120 meters/s) and submitted herein as an example.

FIG. 1 represents a front view of a two-wheel sensor.
FIG. 2 represents a side view of a two-wheel sensor.
FIG. 3 represents a side view of a flexible strip sensor.

FIGS. 1 and 2 represent an adhesion measuring sensor, the sensing element of which consists of two wheels 1 and 2, mounted on fluid film bearings 3 and in contact with the material 4, of a device 5 for measuring the rotational speed of wheel 1, and of a device 6 for braking wheel 2

FIG. 3 represents an adhesion measuring sensor with a sensing element consisting essentially of a flexible strip 7, one end 7a of which is secured to a swivelling support 8 and the other end 7b of which rests on the material 4 moving past, and of a movie camera 9.

Pursuant to this invention, an associated computer performs certain functions, in particular providng active energy to the sensors, displaying the measurement results and, whenever necessary, storing or printing these results. In the event of a failure, the computer can trigger an alarm and have the reqisite corrections carried out on the production or surface treatment facility.

In the application example given of corona conduction treatment on plastic films, the device can be used to control the generator as a function of the measurement.

The computer also embodies a register or programming for measurement calibration relative to other conventional types of measurement. In this method, the material surface condition is analyzed conventionally using existing methods; based on the sensor, the computer then analyzes the same surface on its initial pass, recording the measurement as a reference value for the succeeding measurements. This technique thus provides a comparative and relative measurement.

These measurements are realized by an active and non-destructive sensor, as represented in FIGS. 1 and 2 of the enclosed drawings, or by an active and non-destructive sensor, as represented in FIG. 3.

In the first embodiment, the sensing element of the sensor comprises two independent wheels 1 and 2, mounted on the fluid film bearing 3 and rolling on the material 4, the surface of which is being controlled. The two wheels 1 and 2 are exactly identical in terms of their size, their weight and the surface condition of their running threads. The rotational speed and braking load of the two wheels are measured and transmitted to the associated computer, which derives the surface condition from the difference in the rotational speeds of the two wheels for a given braking torque. The devices 5 and 6 measure the differential rotational speeds of wheels 1 and 2 at a given braking torque, which is determined by means of a system integrated in the rotational speed measuring device 6 of wheel 2. One of the wheels 2 is braked by an adjustable system which allows the torque applied to be checked, for example by means of eddy currents.

As soon as wheel 2, subject to braking, slips and the associated differential speed measurements are made, the braking load is released to allow the two wheels to attain the same speed again. Braking is then re-applied and progressively increased until slipping recurs. In this way the surface condition is controlled sequentially.

Wheel 1 is thus completely free whereas wheel 2 is progressively braked and the value of its corresponding braking torque is instantaneously transmitted to the computer. At a given time, the progressive braking causes wheel 2 to slip on the surface of the material 4 moving past, resulting in a difference between the rotational speeds of wheels 1 and 2. The reading of the braking torque, induced at this time by the brake, provides an indication of the relative value of adhesion and thus of the surface condition. At this intent wheel 2 is freed until the next measurement.

The principle of the measurement is therefore to determine the difference in the rotational speeds of wheels 1 and 2 and the braking torque applied to wheel 2. Due to the braking, wheel 2 exceeds the limit of its braking friction and thus begins to slip, thereby attaining a rotational speed that differs from that of wheel 1. For a given value of the surface condition on the running threads of wheels 1 and 2 and for a given brkaing torque, this difference is representative of the material surface condition. This value is transmitted to the computer and the brake is then released so that wheel 2 can reach its normal operating speed.

In the second embodiment, the sensing element of the sensor consists of a strip 7, one end 7b of which rubs on the surface of the material 4 moving past and whose angular deflection is measured and transmitted to the associated computer.

Depending on the surface condition of roughness, the strip 7 will deflect in consequence. All that is required is to read this deflection, using for example an electronic camera 9, which will transmit this information to the associated computer for use as in the previous embodiment. The device may be calibrated beforehand by rotation of a swivelling support 8, in the appropriate direction, in order to vary the contact pressure at the end 7b of strip 7 on the surface of the material 4.

I claim:

1. A device for measuring the surface condition of material, comprising:
   an adhesion measuring sensor having a sensing element maintained in contact with a surface of the material to be measured and which moves relative to the surface thereof, said sensing element including two independent wheels having running treads in the same surface condition, one of said wheels being unrestrained and the other of said wheels being operatively coupled to a progressively acting brake;
   means for measuring the rotational speeds of the wheels and the braking torque;
   a computer means operatively coupled to said adhesion measuring sensor; and
   means for transmitting said rotational speeds of the wheels and said braking torque to said computer means, said computer means including means for performing comparative measurements from said speeds of the wheels and the braking torque transmitted thereto, and means for displaying the results of said comparative measurements.

2. A device pursuant to claim 1, wherein the independent wheels are mounted on fluid film bearings.

3. A device pursuant to claim 1, wherein one of these wheels is braked by an adjustable system allowing torque control by eddy currents.

4. A device for controlling the surface condition of materials comprising:
   an adhesion measuring sensor including two independent wheels maintained in contact with the surface of the material to be measured and which move relative to the surface, the running treads of said wheels being in the same surface condition, one of said wheels being unrestrained and the other of said wheels being operatively coupled to a progressively acting brake;
   means for measuring the rotational speeds of the wheels and the braking torque; and
   means for transmitting said rotational speed and braking torque to an associated computer, said computer including means for measuring the adhesion from the differential measurement of the rotational speeds of the wheels for a known braking torque and means for controlling surface treatment in response to the measured adhesion.

5. A device as in claim 4, wherein the independent wheels are mounted on fluid film bearings.

6. A device as in claim 4, wherein one of said wheels is braked by an adjustable system allowing torque control by eddy curents.

7. A device as in claim 4, wherein as soon as said wheel subjected to braking slips and said means for measuring measures the associated differential speed, the braking load is released to allow said first and second wheels to attain the same speed and braking is then reapplied and progressively increased until slipping recurs.

8. A device pursuant to claim 4, wherein the surface condition is controlled solely on the basis of the differential measurement of the rotational speeds of the wheels for a known braking torque.

9. A device pursuant to claim 8, wherein, as soon as wheel 1, subject to braking, slips and the associated differential speed measurements are made, the braking load is released to allow the two wheels to attain the same speed again, braking is then re-applied and progressively increased until slipping recurs.

* * * * *